(12) United States Patent
van der Kouwe et al.

(10) Patent No.: US 8,831,703 B2
(45) Date of Patent: Sep. 9, 2014

(54) SELECTIVE MR IMAGING OF SEGMENTED ANATOMY

(75) Inventors: Andre van der Kouwe, Woburn, MA (US); Bruce Fischl, Cambridge, MA (US); Lawrence Wald, Cambridge, MA (US)

(73) Assignee: The General Hospital Corporation, Boston, MA (US)

( * ) Notice: Subject to any disclaimer, the term of this patent is extended or adjusted under 35 U.S.C. 154(b) by 1994 days.

(21) Appl. No.: 11/977,153

(22) Filed: Oct. 23, 2007

(65) Prior Publication Data

US 2008/0103383 A1 May 1, 2008

Related U.S. Application Data

(60) Provisional application No. 60/853,671, filed on Oct. 23, 2006.

(51) Int. Cl.
| | | |
|---|---|---|
| *A61B 5/05* | (2006.01) | |
| *G01R 33/56* | (2006.01) | |
| *A61B 5/055* | (2006.01) | |
| *G01R 33/3415* | (2006.01) | |
| *G01R 33/54* | (2006.01) | |

(52) U.S. Cl.
CPC ............... *A61B 5/055* (2013.01); *G01R 33/56* (2013.01); *G01R 33/3415* (2013.01); *G01R 33/5608* (2013.01); *G01R 33/543* (2013.01)
USPC ........... 600/410; 324/309; 324/307; 600/407; 382/128

(58) Field of Classification Search
USPC .......... 324/300, 306, 307, 309; 600/410, 411, 600/416, 417, 424
See application file for complete search history.

(56) References Cited

U.S. PATENT DOCUMENTS

| | | | | |
|---|---|---|---|---|
| 5,072,182 A * | 12/1991 | Derby et al. | ................. | 324/309 |
| 5,859,891 A * | 1/1999 | Hibbard | ........................... | 378/62 |
| 5,912,557 A * | 6/1999 | Wilman et al. | ............... | 324/309 |
| 5,926,022 A * | 7/1999 | Slavin et al. | .................. | 324/309 |
| 6,021,213 A | 2/2000 | Helterbrand et al. | | |
| 6,037,771 A * | 3/2000 | Liu et al. | ....................... | 324/309 |
| 6,057,680 A * | 5/2000 | Foo et al. | ....................... | 324/206 |
| 6,195,409 B1 * | 2/2001 | Chang et al. | .................... | 378/20 |
| 6,259,940 B1 * | 7/2001 | Bernstein et al. | ............. | 600/410 |
| 6,275,035 B1 * | 8/2001 | Debbins et al. | ............... | 324/307 |
| 6,307,369 B1 * | 10/2001 | Felmlee et al. | ............... | 324/309 |

(Continued)

OTHER PUBLICATIONS

Van der Kouwe et al, "On-line automatic slice positioning for brain MR imaging", NeuroImage 27 (2005) 222-230.*

(Continued)

*Primary Examiner* — Nicholas Evoy
(74) *Attorney, Agent, or Firm* — Quarles & Brady, LLP

(57) ABSTRACT

A system and method for performing an MRI or MRS scan that is optimized for a particular target structure. A prescan is conducted during a first session in which an image that is optimized for segmentation is acquired along with an alignment scout image or a 2D or 3D navigator signal. The segmentation process is employed to locate and define the target structure. During a second session the alignment scout image or navigator signal is reacquired and the information is used to determine the position transformation needed to align images from the two sessions. The position transformation information and the segmentation information are then employed to tailor a prescribed pulse sequence to examine the target structure.

17 Claims, 9 Drawing Sheets

(56) References Cited

U.S. PATENT DOCUMENTS

| | | | |
|---|---|---|---|
| 6,310,479 B1* | 10/2001 | Zhu et al. | 324/312 |
| 6,366,797 B1* | 4/2002 | Fisher et al. | 600/410 |
| 6,381,486 B1* | 4/2002 | Mistretta et al. | 600/420 |
| 6,516,210 B1* | 2/2003 | Foxall | 600/410 |
| 6,618,605 B1* | 9/2003 | Wolff et al. | 600/410 |
| 6,618,607 B2* | 9/2003 | Song | 600/410 |
| 6,670,811 B2* | 12/2003 | Wind et al. | 324/307 |
| 6,717,406 B2* | 4/2004 | Sodickson | 324/307 |
| 6,734,672 B2* | 5/2004 | Feiweier | 324/309 |
| 6,791,321 B2* | 9/2004 | Willig-Onwuachi et al. | 324/309 |
| 6,795,723 B1* | 9/2004 | Liu | 600/410 |
| 6,798,202 B2* | 9/2004 | Savelainen | 324/318 |
| 6,801,037 B1* | 10/2004 | Zhang | 324/307 |
| 6,845,260 B2* | 1/2005 | Liu et al. | 600/410 |
| 6,845,261 B2* | 1/2005 | Pettersson et al. | 600/413 |
| 6,889,071 B2* | 5/2005 | Saranathan et al. | 600/413 |
| 6,903,548 B2* | 6/2005 | Foo | 324/306 |
| 6,952,097 B2* | 10/2005 | Schreck et al. | 324/309 |
| 6,956,373 B1* | 10/2005 | Brown et al. | 324/309 |
| 6,958,605 B2* | 10/2005 | Dale et al. | 324/307 |
| 6,965,232 B2* | 11/2005 | Sodickson | 324/307 |
| 7,049,816 B2* | 5/2006 | Mistretta et al. | 324/309 |
| 7,075,299 B1* | 7/2006 | Peters | 324/309 |
| 7,081,750 B1* | 7/2006 | Zhang | 324/309 |
| 7,081,751 B2* | 7/2006 | Twieg | 324/310 |
| 7,082,325 B2* | 7/2006 | Hashimshony et al. | 600/411 |
| 7,098,662 B2* | 8/2006 | Hinks et al. | 324/318 |
| 7,102,352 B2* | 9/2006 | Hinks et al. | 324/318 |
| 7,123,008 B1* | 10/2006 | Damadian et al. | 324/309 |
| 7,145,336 B2* | 12/2006 | Brown | 324/309 |
| 7,358,732 B2* | 4/2008 | Van Der Kouwe et al. | 324/309 |
| 7,432,706 B2* | 10/2008 | van der Kouwe | 324/306 |
| 7,450,983 B2* | 11/2008 | Weiss | 600/410 |
| 7,602,179 B2* | 10/2009 | van der Kouwe et al. | 324/307 |
| 2002/0172408 A1* | 11/2002 | Saito et al. | 382/132 |
| 2003/0139659 A1* | 7/2003 | Dale et al. | 600/407 |
| 2004/0204644 A1* | 10/2004 | Tsougarakis et al. | 600/410 |
| 2005/0043614 A1* | 2/2005 | Huizenga et al. | 600/427 |
| 2005/0088177 A1* | 4/2005 | Schreck et al. | 324/307 |
| 2005/0165294 A1* | 7/2005 | Weiss | 600/410 |
| 2005/0190955 A1* | 9/2005 | Brown | 382/128 |
| 2009/0123384 A1* | 5/2009 | Wald et al. | 424/9.32 |

OTHER PUBLICATIONS

Fischl et al, "Sequence-independent segmentation of magnetic resonance images", NeuroImage 23 (2004) S69-S84.*

Jovicich et al, "Reliability in multi-site structural MRI studies: Effects of gradient non-linearity correction on phantom and human data", NeuroImage 30 (2006) 436-443.*

Benner et al, "Comparison of Manual and Automatic Section Positioning of Brain MR Images" Radiology: vol. 239: No. 1—Apr. 2006.*

* cited by examiner

SELECTIVE MR IMAGING OF SEGMENTED ANATOMY

REFERENCE TO RELATED APPLICATIONS

The present patent application claims benefit of provisional U.S. patent application Ser. No. 60/853,671 filed Oct. 23, 2006, and entitled SELECTIVE MR IMAGING OF SEGMENTED ANATOMY.

STATEMENT REGARDING FEDERALLY SPONSORED RESEARCH

N/A

BACKGROUND OF THE INVENTION

The present invention relates generally to nuclear magnetic resonance imaging (MRI) and magnetic resonance spectroscopy (MRS) and, more particularly, to prescribing pulse sequences for an MRI or MRS system that precisely target a selected structure to be examined.

When a substance such as human tissue is subjected to a uniform magnetic field (polarizing field $B_0$), the individual magnetic moments of the spins in the tissue attempt to align with this polarizing field, but precess about it in random order at their characteristic Larmor frequency. If the substance, or tissue, is subjected to a magnetic field (excitation field $B_1$) which is in the x-y plane and which is near the Larmor frequency, the net aligned moment, Mz, may be rotated, or "tipped", into the x-y plane to produce a net transverse magnetic moment Mt. A NMR signal is emitted by the excited spins after the excitation signal $B_1$ is terminated, this signal may be received and processed to form an image. The RF excitation pulse that produces this $B_1$ excitation field can be prescribed to excite well defined structures in the subject of the examination.

When utilizing these NMR signals to produce images, magnetic field gradients ($G_x$, $G_y$ and $G_z$) are employed. Typically, the region to be imaged is scanned by a sequence of measurement cycles in which these gradients vary according to the particular localization method being used. The resulting set of received NMR signals are digitized and processed to reconstruct an image using one of many well known reconstruction techniques. When using these NMR signals in spectroscopy, the magnetic field gradients are employed along with RF saturation pulses to suppress NMR signals from all tissues except the prescribed structure of interest.

It is desirable when imaging a structure embedded in other anatomy to prescribe a pulse sequence that will optimize a scan parameter such as scan time, image resolution, image SNR, or CNR. Similarly, when acquiring spectroscopy data it is desirable to optimize the scan prescription for the particular structure from which the information is sought. To achieve this, the target structure must first be separately identified, or "segmented", from surrounding tissues. Then, the RF pulses and magnetic field gradients in a chosen pulse sequence must be optimized for the segmented structure.

There are many methods known and used to segment different tissue types or structures in the human body. However, such methods require the acquisition of an image as input to the segmentation process and extensive processing time. Processing times measured in hours are required using present technology. As a result, it is not practical to prescribe imaging or spectroscopy scans that are optimized for a particular structure because the prescan and segmentation steps that precede the scan are too lengthy.

SUMMARY OF THE INVENTION

The present invention overcomes the aforementioned drawbacks by providing a system and method for performing an MRI or MRS scan that is optimized for a particular target structure. A prescan is conducted during a first session in which an image that is optimized for segmentation is acquired along with an alignment scout image or a 2D or 3D navigator signal. The segmentation process is employed to locate and define the target structure. During a second session the alignment scout image or navigator signal is reacquired and the information is used to determine the position transformation needed to align images from the two sessions. The position transformation information and the segmentation information are then employed to tailor a prescribed pulse sequence to examine the target structure.

The present invention allows RF pulses employed in a prescribed pulse sequence to be tailored to a selected target structure. The target structure is selected using the segmentation information and the system produces RF pulses that will excite the tissues in the target structure. Multiple transmit coils may be used to shape the excited region to correspond with the current location of the target structure. In addition, this same information may be used to produce RF saturation pulses that saturate spins in regions surrounding the target structure so that signals therefrom are suppressed.

DESCRIPTION OF THE PREFERRED EMBODIMENT

Figure 1:
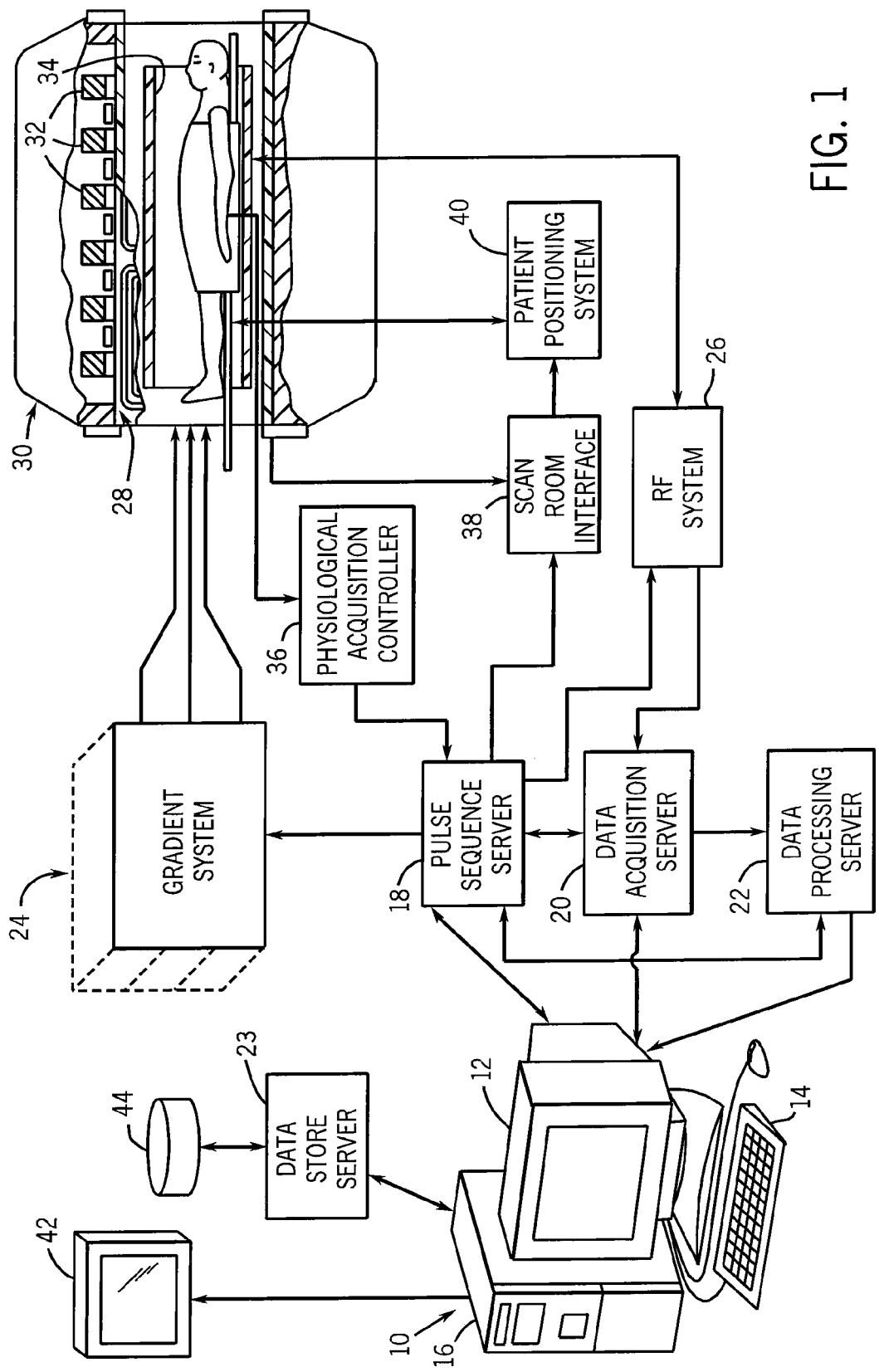
FIG. 1 is a block diagram of an MRI system which employs the present invention.

Referring particularly to FIG. 1, the preferred embodiment of the invention is employed in an MRI system manufactured by Siemens Medical Solution of Erlangen, Germany. The MRI system includes a workstation 10 having a display 12 and a keyboard 14. The workstation 10 includes a processor 16 which is a commercially available programmable machine running a commercially available operating system. The workstation 10 provides the operator interface which enables scan prescriptions to be entered into the MRI system.

The workstation 10 is coupled to four servers: a pulse sequence server 18; a data acquisition server 20; a data processing server 22, and a data store server 23.

The pulse sequence server 18 functions in response to program elements downloaded from the workstation 10 to operate a gradient system 24 and an RF system 26. Gradient waveforms necessary to perform the prescribed scan are produced and applied to the gradient system 24 which excites gradient coils in an assembly 28 to produce the magnetic field gradients $G_x$, $G_y$ and $G_z$ used for position encoding NMR signals. The gradient coil assembly 28 forms part of a magnet assembly 30 which includes a polarizing magnet 32 and a whole-body RF coil 34.

RF excitation waveforms are applied to the RF coil 34 by the RF system 26 to perform the prescribed magnetic resonance pulse sequence. Responsive NMR signals detected by a separate RF coil array described below are received by the RF system 26, amplified, demodulated, filtered and digitized under direction of commands produced by the pulse sequence server 18. The RF system 26 includes an RF transmitter for producing a wide variety of RF pulses used in MR pulse sequences. The RF transmitter is responsive to the scan prescription and direction from the pulse sequence server 18 to produce RF pulses of the desired frequency, phase and pulse amplitude waveform.

The RF system 26 also includes a plurality of RF receiver channels. In the preferred embodiment 12 receiver channels are employed although any number of receive channels may be employed depending on the receive coil array being used. Each RF receiver channel includes an RF amplifier that amplifies the NMR signal received by the coil to which it is connected.

The pulse sequence server 18 also optionally receives patient data from a physiological acquisition controller 36. The controller 36 receives signals from a number of different sensors connected to the patient, such as ECG signals from electrodes or respiratory signals from a bellows. Such signals are typically used by the pulse sequence server 18 to synchronize, or "gate", the performance of the scan with the subject's respiration or heart beat.

The pulse sequence server 18 also connects to a scan room interface circuit 38 which receives signals from various sensors associated with the condition of the patient and the magnet system. It is also through the scan room interface circuit 38 that a patient positioning system 40 receives commands to move the patient to desired positions during the scan.

The digitized NMR signal samples produced by the RF system 26 are received by the data acquisition server 20. The data acquisition server 20 operates to receive the real-time NMR data and provide buffer storage such that no data is lost by data overrun. In some scans the data acquisition server 20 does little more than pass the acquired NMR data to the data processor server 22. However, in scans which require information derived from acquired NMR data to control the further performance of the scan, the data acquisition server 20 is programmed to produce such information and convey it to the pulse sequence server 18. For example, during prescans NMR data is acquired and used to calibrate the pulse sequence performed by the pulse sequence server 18. Also, navigator signals may be acquired during a scan and used to adjust RF or gradient system operating parameters or to control the view order in which k-space is sampled. And, the data acquisition server 20 may be employed to process NMR signals used to detect the arrival of contrast agent in an MRA scan. In all these examples the data acquisition server 20 acquires NMR data and processes it in real-time to produce information which is used to control the scan.

The data processing server 22 receives NMR data from the data acquisition server 20 and processes it in accordance with an image reconstruction method. Images reconstructed by the data processing server 22 are conveyed back to the workstation 10 where they are stored. Real-time images may be output to operator display 12 or a display 42 which is located near the magnet assembly 30 for use by attending physicians. Batch mode images or selected real time images are stored in a host database on disc storage 44. The workstation 10 may be used by an operator to archive the images, produce films, or send the images via a network to other facilities.

Figure 2:
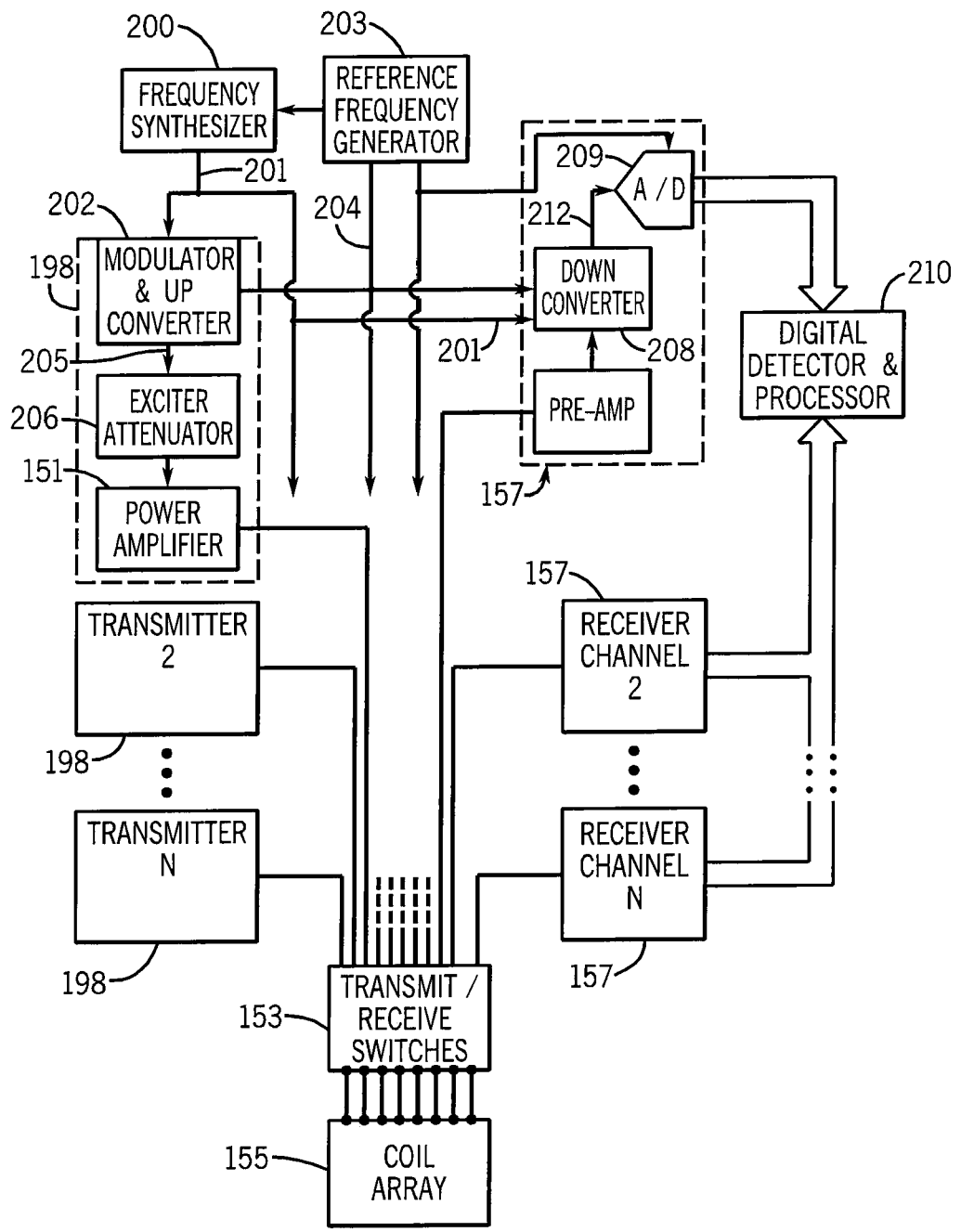
FIG. 2 is a block diagram of a transceiver which forms part of the MRI system of FIG. 1.

Referring particularly to FIG. 2, the RF system 26 includes a set of transmitters 198 that each produce a prescribed rf excitation field. The base, or carrier, frequency of this RF excitation field is produced under control of a frequency synthesizer 200 which receives a set of digital signals from the pulse sequence server 18. These digital signals indicate the frequency and phase of the RF carrier signal produced at an output 201. The RF carrier is applied to a modulator and up converter 202 in each transmitter 198 where its amplitude is modulated in response to a signal R(t) also received from the pulse sequence server 18. The signal R(t) defines the envelope, or waveform, of the RF excitation pulse to be produced and is produced by sequentially reading out a series of stored digital values. These stored digital values may, be changed to enable any desired RF pulse envelope, or waveform, to be produced by each transmitter 198. The RF pulses produced by the transmitters 198 can thus be separately controlled by the pulse sequence server 18. The phase and amplitude can be controlled to achieve $B_1$ shimming and the waveforms can be shaped and played out simultaneously with gradient waveforms to implement Transmit SENSE.

The magnitude of the RF excitation pulse produced at output 205 is attenuated by an exciter attenuator circuit 206 in each transmitter which also receives a digital command from the pulse sequence server 18. The attenuated RF excitation pulses are applied to a power amplifier 151 in each transmitter 198. The power amplifiers are current source devices that connect to respective transmit inputs on a set of transmit/receive switches 153. The transmitters 198 are connected through transmit/receive switches 153 to separate coil elements in a coil array 155.

Referring still to FIG. 2 the signal produced by the subject is picked up by the coil array 155 and applied to the inputs of a set of receive channels 157. A preamplifier 160 in each receiver cannel 157 amplifies the signal by an amount determined by a digital attenuation signal received from the pulse sequence server 18. The received signal is at or around the Larmor frequency, and this high frequency signal is down converted in a two step process by a down converter 208 which first mixes the NMR signal with the carrier signal on line 201 and then mixes the resulting difference signal with a reference signal on line 204. The down converted NMR signal is applied to the input of an analog-to-digital (A/D) converter 209 which samples and digitizes the analog signal and applies it to a digital detector and signal processor 210 which produces 16-bit in-phase (I) values and 16-bit quadrature (Q) values corresponding to the received signal. The resulting stream of digitized I and Q values of the received signal are output to the data acquisition server 20. The reference signal as well as the sampling signal applied to the A/D converter 209 are produced by a reference frequency generator 203.

The transmit/receive switches 153 are operated by the pulse sequence server 18 to connect the transmitters 198 to the coil elements in the coil array 155 during those parts of the pulse sequence in which an rf magnetic field is to be produced. Each transmitter 198 is separately controlled by the pulse sequence server 18 to produce an rf field of a prescribed amplitude, frequency, phase and envelope at each of the coil elements. The combined rf fields of the coil elements produce the prescribed $B_1$ field throughout the region of interest in the subject being imaged. Each transmitter 198 is also separately controlled to play out a pulse envelope, or waveform, while driving the gradient coils with waveforms that implement Transmit SENSE.

When the $B_1$ field is not produced the pulse sequence server 18 operates the transmit/receive switches 153 to connect each of the receive channels to the respective coil elements. Signals produced by excited spins in the subject are picked up and separately processed as described above.

Figure 3:
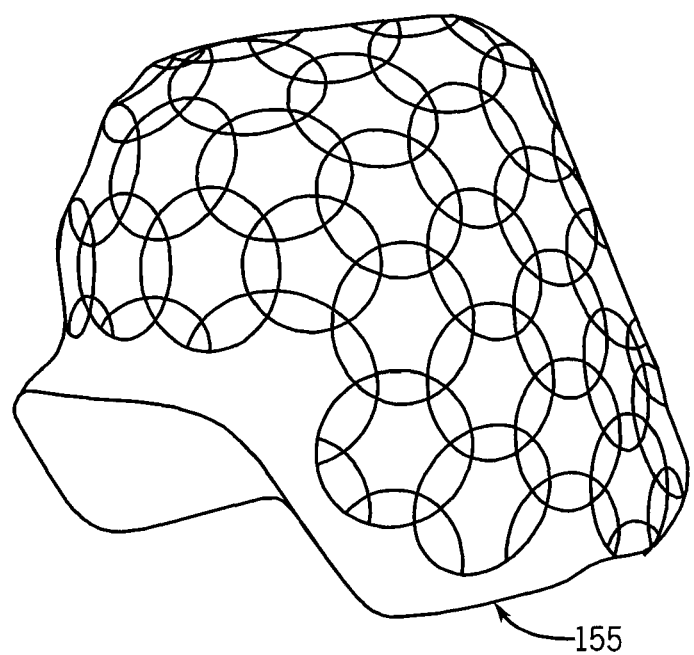
FIG. 3 is a perspective view of a coil array for use with the transceiver of FIG. 2 to image structures in the head of a subject.

One embodiment of the coil array 155 is shown in FIG. 3. The close-fitting fiberglass helmet structure of the array 155 is modeled after the European head standard from EN960/1994 for protective headgear. This coil array 155 has separate RF coil elements which are positioned over the curved helmet surface. Each coil element is substantially circular in shape and adjacent coil elements overlap such that their mutual inductance is minimized. As described in co-pending PCT application WO 2005/109010A2 filed on May 3, 2005 and entitled "Coil Array Positioning", inductive coupling between coil elements is reduced by overlapping adjacent coil elements and using preamplifier decoupling. The cable leading from each of the coil elements through the transmit/receive switch to the preamplifier in its corresponding receiver channel is carefully chosen and the tuning of the matching circuit to the preamplifier is chosen to transform the high preamplifier input impedance to a low impedance across the circular coil element. An arrangement of hexagonal and pentagonal tiles cover the helmet surface, similar to a geodesic tiling of a sphere. Each tile has sides that are approximately 23 mm long although it was necessary to distort the pentagonal tiles in places in order to map them onto the surface of the helmet. A circular surface coil is centered on each one of the tiles. Each surface coil is made from 0.031 inch thick G10 copper clad circuit board with a conductor width of 2.5 mm. The diameter of each coil element ranges from 4.5 cm to 5.5 cm. It has been found that significant 5 to 8-fold gains in SNR are possible with this structure as compared to conventional head coils, particularly in the cerebral cortex.

The technology of receive coil arrays is well developed as described above, and relies on the techniques of preamp decoupling, which reduces coupling between coil elements by minimizing the currents which can flow in the coil elements. This technique can not be applied in the case of a transmit coil array because a flow of current in the coil elements is necessary to create a $B_1$ field with the device. This means that coupling between the coil elements is much more problematic in a transmit array. One of the main techniques for reducing coupling between coil elements is to overlap them to null their mutual inductance. The coil design described above allows the critical overlap to be maintained between all neighboring coils even for a domed design which conforms closely to the shape of the human head. Coupling between neighboring coils is also minimized through the use of capacitive or inductive decoupling networks. Coupling between any coil pair (including non-neighboring coils) can also be reduced through the use of current source amplifiers 151 for each element. Also, the use of shielded or "stripline" coil elements may be used to reduce coupling between neighboring coil elements.

Distributing the coil elements all over the surface of the head provides greater flexibility in controlling the $B_1$ profile created by the coil, either through adjustment of the waveform, phase and amplitude of the RF signal sent to each coil element, or through the use of different coil elements over the surface of the head. Transmit elements may be similarly arranged to provide greater flexibility in controlling the $B_1$ field created by the transmission elements. Also, the coils may provide both transmit and receive functionality.

The MRI system is used in two separate sessions to practice the one embodiment of the invention. The first session is a segmentation session and the second session is an imaging session. The steps employed in the segmentation session are set forth in FIG. 4 and the steps employed in the imaging session are set forth in FIG. 5.

Figure 4:
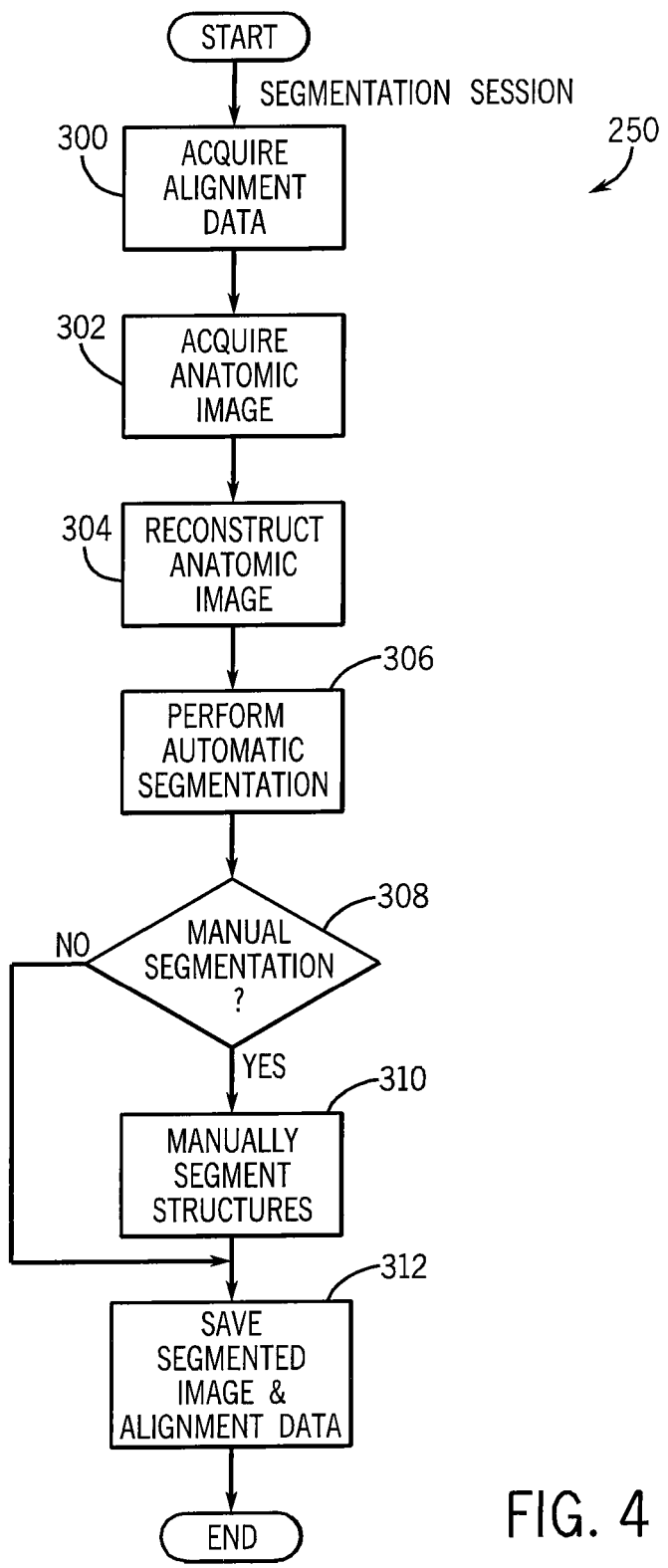
FIG. 4 is a flow chart of the steps performed during a segmentation session using the MRI system of FIG. 1.

Referring to FIG. 4, the first step in the segmentation session 250 is to acquire alignment data as indicated at process block 300. In one embodiment, the scout scan serves as input to the Atlas/AutoAlign procedure on a Siemens MRI system. This AutoAlign scout and associated registration procedure yields a registration matrix that relates the scanner coordinate system to the AutoAlign atlas space. While both coordinate systems are defined anatomically as "LPS" (left-posterior-superior) systems, AutoAlign space is a truly anatomical coordinate system since it is defined by registration with an anatomical atlas constructed by combining hundreds of aligned brain volumes. The scanner coordinate system relies on the subject being placed exactly in a defined position on the scanner table (usually supine), and it is rarely the case that the true anatomical axes of the brain align precisely with the scanner axes. We therefore relate scanner LPS coordinates to "true" anatomical LPS coordinates by means of an AutoAlign matrix $M_{AA}^{seg}$.

$$v_{AA/LPS} = (M_{AA}^{seg})^{-1} v_{LPS}^{seg}. \quad (1)$$

Other alignment data may be acquired and used to register images acquired during the two sessions. For example, a spherical navigator signal may be acquired and saved along with the segmented image or a low resolution image may be acquired and saved.

The next step indicated at process block 302 is to acquire an anatomic image or images that enable the various tissue types to be clearly distinguished. In one embodiment, an MPRAGE pulse sequence and protocol, such as that described by Xiao Han, Jorge Jovicich, David Salat, Andre van der Kouwe, Brian Quinn, Silvester Czanner, Evelina Busa, Jenni Pacheco, Marilyn Albert, Ronald Killiany, Paul Maguire, Diana Rosas, Nikos Makris, Anders Dale, Bradford Dickerson, and Bruce Fischl "Reliability of MRI-derived measurements of human cerebral cortical thickness: The effects of field strength, scanner upgrade and manufacturer", NeuroImage, 32(1):180-194, (2006), is used. An anatomic image is reconstructed from the acquired data as indicated at process block 304 and the reconstructed image is transferred to a separate work station where an automatic segmentation process is performed as indicated at process block 306. The image reconstruction is conventional and the automatic segmentation is performed by a freely available software package called "FreeSurfer" (http://surfer.nmr.mgh.harvard.edu). The segmentation process takes several hours, and usually completes without supervision if the anatomic images are of sufficient quality. The coordinate system used by FreeSurfer to index the segmented volume is a "CRS" (column-row-slice) system. This relates to the scanner LPS coordinate system through a matrix $M_{CRS \rightarrow LPS}^{seg}$ determined from the scanner prescription by FreeSurfer (FreeSurfer actually provides an RAS transformation that is easily converted to an LPS transformation).

$$v_{LPS}^{seg} = M_{CRS \rightarrow LPS}^{seg} v_{CRS}^{seg}. \quad (2)$$

When the automatic segmentation is completed the operator may elect at decision block 308 to manually select additional structures as indicated at process block 310. For example, a tumor depicted in the anatomic image may be manually selected by moving a cursor around its boundary using a computer mouse or a track ball. Alternatively, it is contemplated that selection may be done without any automatic segmentation step and, instead, a fully manual segmentation process is performed.

Figure 6:
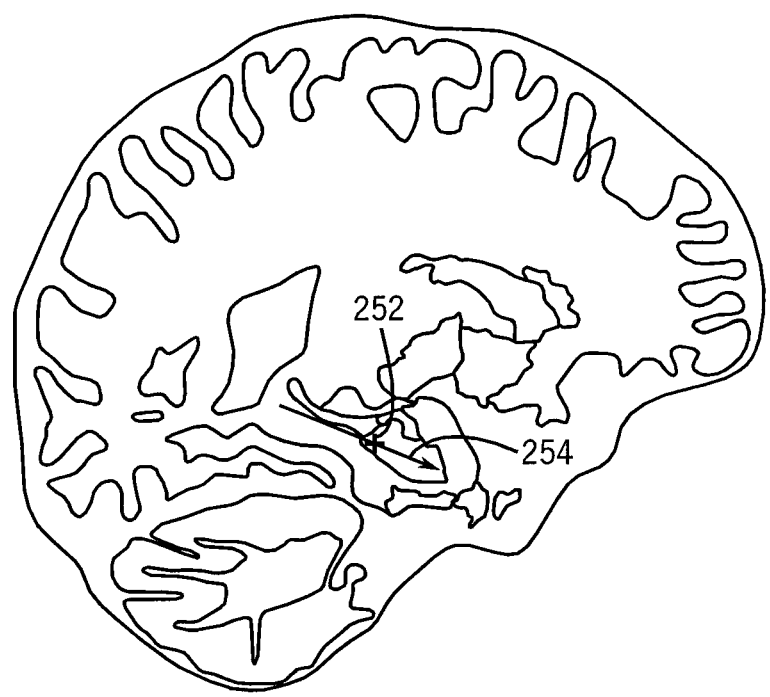
FIG. 6 is a segmented image of a brain volume in accordance with the present invention.

As indicated at process block 312, the segmentation session ends by saving the segmentation information and the alignment data. The segmentation information includes a segmented image produced, for example, by FreeSurfer. Such an image is illustrated in FIG. 6 where the subject is the human brain with cortical regions and subcortical structures labeled by FreeSurfer. In the image, a cursor 252 denotes the centroid of the right hippocampus, and an arrow 254 denotes the projection of the principal eigenvector in the sagittal plane (this eigenvector has a small through-plane component). Regions are also labeled numerically according to a lookup table (LUT) that relates the label number to a structure name. The volume header contains the alignment data which includes the AutoAlign matrix and segmentation image CRS to scanner LPS matrix.

If AutoAlign is not used for alignment purposes, the navigator signal or low resolution alignment image is stored with the segmentation information.

Due to the length of time needed to segment the anatomic image, the patient is removed from the scanner after the anatomic image and alignment data is acquired during the segmentation session. At a later time, the patient returns to the MRI system for the imaging session. Every effort is made to place the patient in the exact same location and orientation used during the first session.

Figure 5:
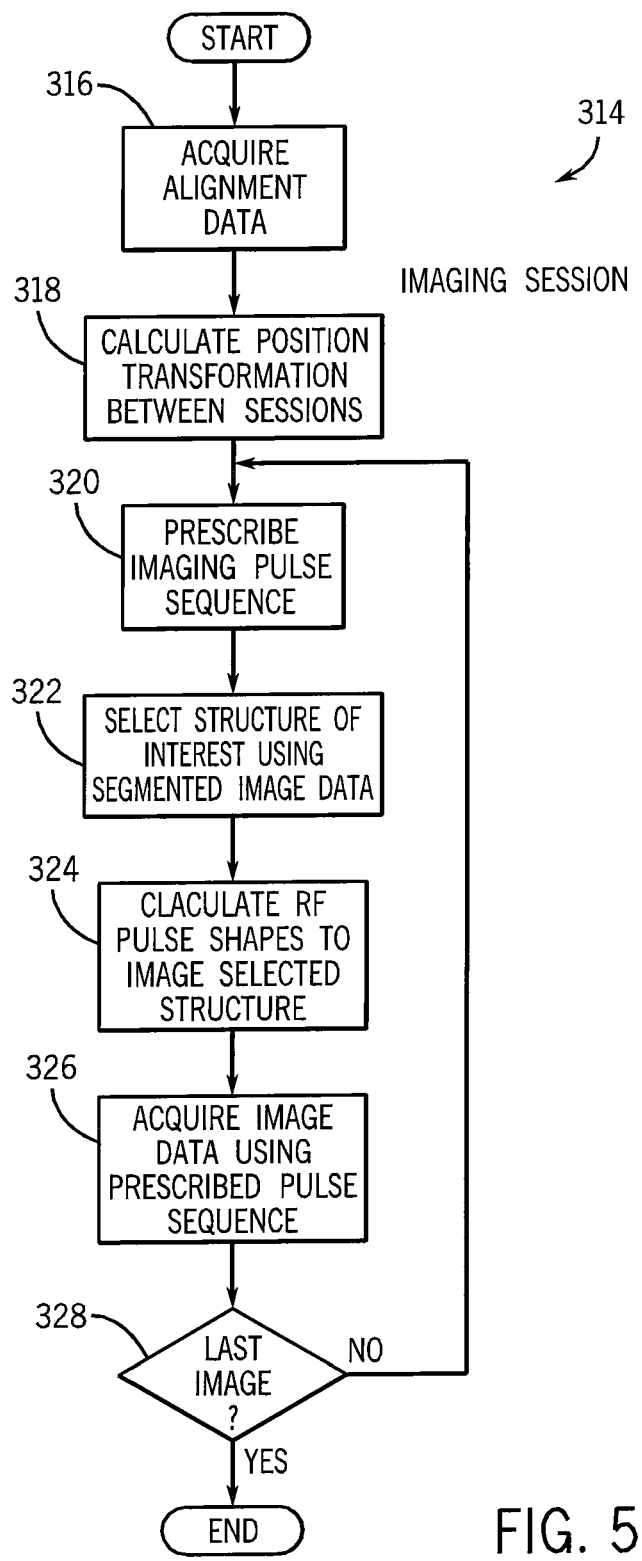
FIG. 5 is a flow chart of the steps performed during an imaging session using the MRI system of FIG. 1.

Referring now to FIG. 5, the imaging session 314 begins by acquiring alignment data as indicated at process block 316. If AutoAlign is used, an AutoAlign matrix $M_{AA}$ is determined. The scanner LPS coordinate system for this session is related to the "true" anatomical LPS coordinates by the AutoAlign matrix.

$$v_{LPS} = M_{AA} v_{AA/LPS}. \quad (3)$$

Positions and orientations in the segmented volume (CRS coordinates) can now be related to scanner LPS coordinates during the imaging session by applying, in order, the transformations in equations (2), (1), and (3) as indicated at process block 318.

If, in the alternative, a navigator signal or low resolution image is used for alignment, such alignment data is acquired at process block 316. This current alignment data is used with the corresponding alignment data acquired during the segmentation session to calculate the position transformation at process block 318.

As indicated at process block 320, the operator selects and prescribes an imaging pulse sequence that is going to be used to acquire image data. Whereas many of the scan parameters such as TE, TR, flip angle, and readout bandwidth may be manually prescribed, it is a feature of the present invention that the location, orientation, and shape of the region of interest (ROI) from which image data is to be acquired is established automatically using the segmented image data as indicated at process block 322.

Figure 7:
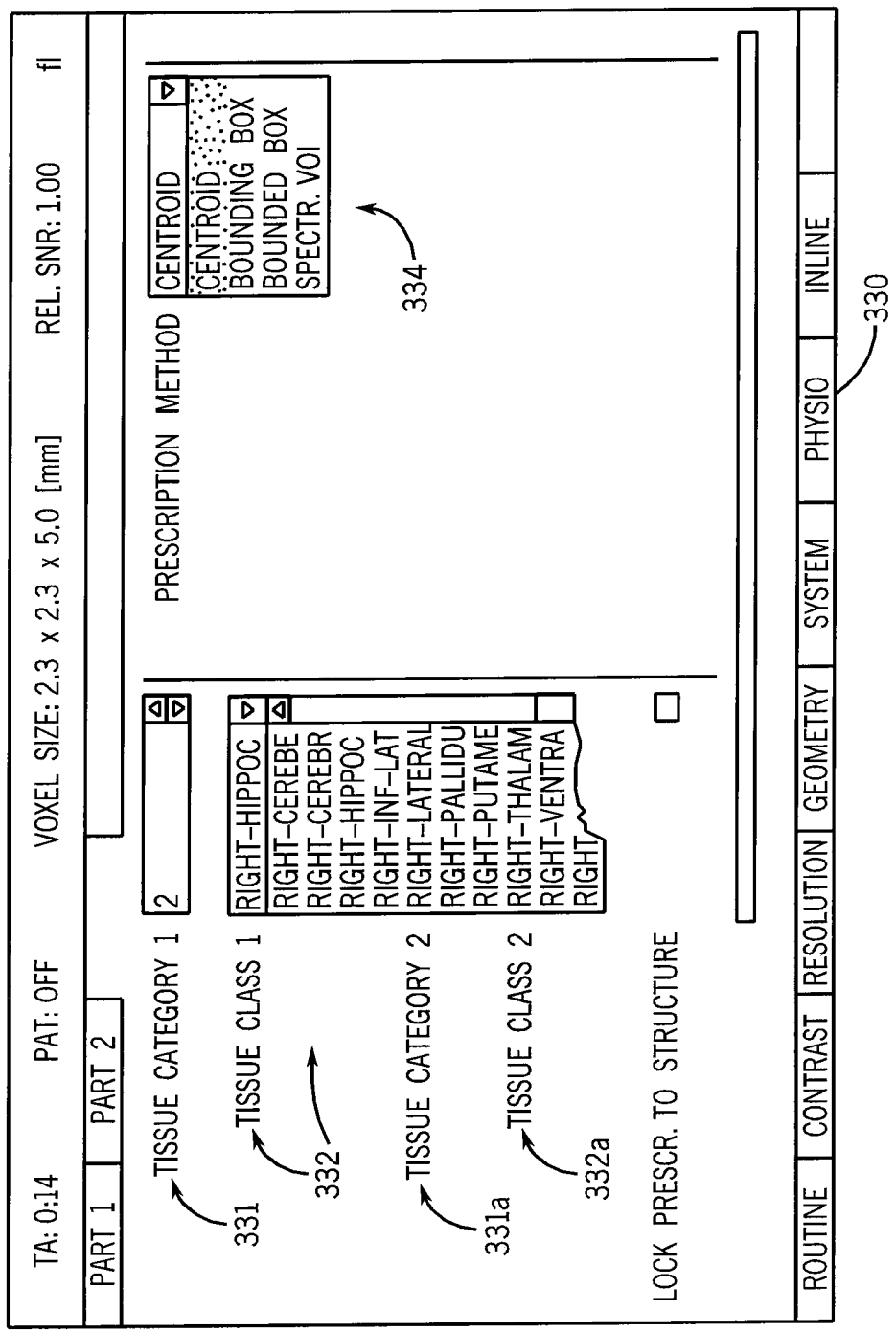
FIG. 7 is a pictorial representation of a display in accordance with the present invention in which a scanner operator can select structure(s) of interest that occur in the current subject's segmented information and select a prescription.

As shown in FIG. 7, a user interface 330 is provided that allows the operator to select the structure or set of structures of interest on the scanner display. In particular, the operator selects a tissue category 331, which narrows an alphabetized subset of the LUT (the subset of structures that actually occur in the specific segmented volume) 332 from which the operator can select the specific desired structures. Additionally, it is contemplated that an operator may select a second tissue category 331a and a second tissue class 332a. The scanner then calculates the slice position or spectroscopy VOI and displays the proposed position to the operator. The position and orientation are calculated using a method selected by the operator from a number options displayed list 334, and the volume of the structure(s) of interest is displayed. As will be described in greater detail below, it is contemplated that four methods may be used to calculate the position, orientation, and shape prescription: centroid; bounding box; bounded box; and minimum projection. Once the volume of the structure(s) of interest is displayed, the operator has the option to manually modify the position and shape before starting the scan.

The centroid method calculates the centroid of the voxels in the selected structure(s), and the center of the scan box is placed at this point. The centroid is equivalent to the center of mass for an object with uniform density, and is numerically equal to the mean of the voxel coordinates. The centroid method also calculates the covariance matrix for the voxel coordinates. The principal eigenvector is considered as the long axis of the structure. The second eigenvector is the wide axis of the structure and the cross product (remaining perpendicular direction) is the short axis. Since this assumes that the structure is Gaussian in shape, it is generally not applicable to brain structures. If any eigenvalues are close to within a small percentage of one another (i.e. the cross-section of the distribution in the plane of the corresponding eigenvectors is close to circular), the order of the eigenvectors is meaningless, and the axes may be snapped to anatomical coordinates.

The bounding box method calculates the smallest arbitrarily oriented box that completely encloses the structure(s) of interest. The method provides the center point of the box, required dimensions, and directions of the long, wide, and short axes. A fast approximate method is given by Barequet and Har-Peled [Barequet, 2001]. This can be used to calculate the most efficient scan prescription for sequences with regular Cartesian excitation and encoding.

Figure 8:
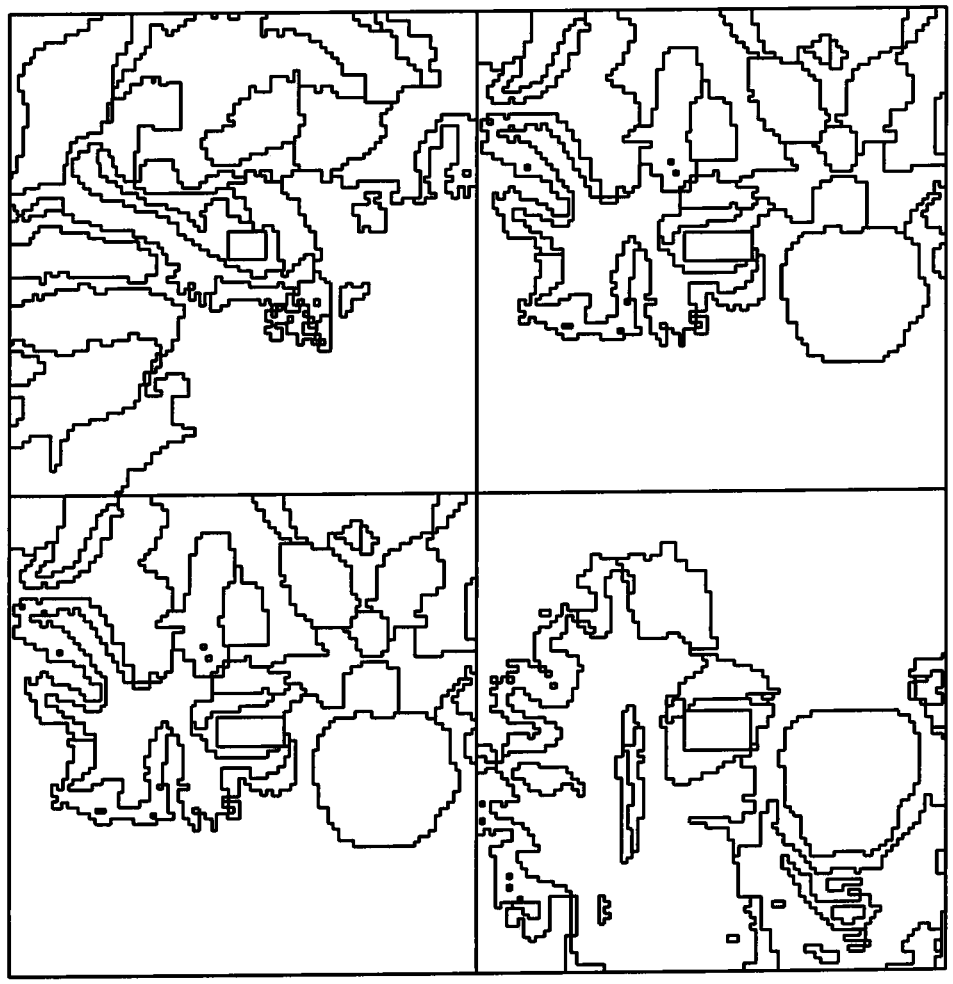
FIG. 8 is segmented images showing the largest bounded box that fits completely within the right hippocampus.

The bounded box method calculates the largest arbitrarily oriented box that is completely enclosed by the boundaries of the structure of interest. This is useful for spectroscopy where it may be important to image metabolites only in a specific structure and not in adjacent structures. FIG. 8 shows a segmented volume with the largest bounded box found using an exhaustive search method that locates the largest bounded box with edges parallel to the coordinate system of the segmentation. The volume of the box and structure are determined, and the ratio calculated as an indication of the efficiency of the prescription for spectroscopy.

Figure 9:
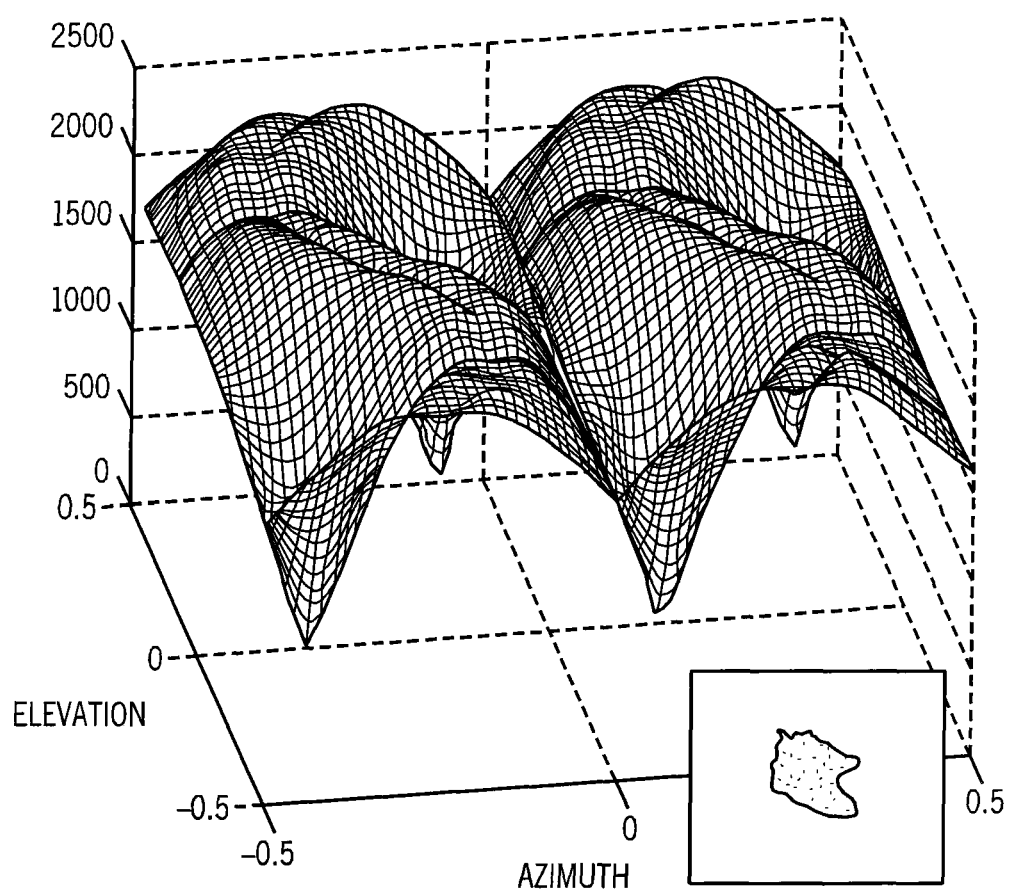
FIG. 9 is a plot of surface area of projection of hippocampus on arbitrary oriented plane vs. azimuth and elevation of plane, rotation angles are given as a fraction of full rotations ($\times 2\pi$ radians).

The minimum projection method calculates the orientation of the plane for which the total area of the projection of the structure of interest is smallest (approximated by the area of the smallest arbitrarily rotated rectangle bounding the projection on the plane). The space was searched using simulated annealing [Kirkpatrick, 1983], as this approach is more robust to settling in local minima. The resulting search space is shown in FIG. 9. Specifically, FIG. 9 shows a plot of surface area of projection of hippocampus on arbitrary oriented plane vs. azimuth and elevation of plane, rotation angles are given as a fraction of full rotations ($\times 2\pi$ radians). The surface repeats at intervals of 0.5 (corresponding to $\pi$ radian rotations). Again, the normal vector to the optimal plane is provided as the long axis, and the wide and short axes are calculated based on the orientation of the bounding rectangle or eigenvectors of the projected distribution in the plane, along with the minimum field of view required in each direction. FIG. 9 shows the projection of hippocampus on optimal plane, rotated to minimize the area of the bounding box.

Apart from the automatic offline segmentation based on the MPRAGE pulse sequence, segmentation can be based on some other sequences designed for a particular purpose. For example, the RF pulses of the standard gradient echo pulse sequence can be modified to select a slab and also be spectrally selective for fat or water. The resulting images can be used as input to the algorithm that automatically places saturation bands or designs the 2D spatial RF pulse for the CSI sequence. An alternative approach that we will explore is to collect a large number of high-bandwidth echoes in a 3D FLASH sequence and analyze the spectrum at each voxel.

Automatic positioning need not be based on segmented anatomy. In some studies, it is the biochemical changes in regions of functional activation that are of interest. The system may determine VOIs based on labeled volumes that are anatomical, functional, hand-drawn, or based on diffusion images. Accordingly, functionally-driven automatic positioning can readily be incorporated in the framework. Conversely, functional information can be determined from a single voxel spectroscopy (SVS) scan, such as estimating T2* from the water line width in the SVS data correlated with stimulus.

As indicated at process block 324 of FIG. 5, after the structure of interest has been selected, the RF pulses in the prescribed pulse sequence are calculated for optimal performance. It is contemplated that this step may be partially or fully completed before the imaging session that will be described below. For example, the waveform for the RF pulse can be calculated offline and then finally modified to take into account the position of the subject during the imaging session. Given the center of the structure or box containing the structure, the center of the slice prescription or spectroscopy VOI is selected at this point. The long axis is chosen to be the readout direction. The short and wide axes may be allocated to phase and readout direction depending on how the rest of the head wraps in the phase encoding direction.

For single voxel spectroscopy, the volume of interest (VOI) is a rectanguloid bounded in all directions by saturation bands, so the order of axes is arbitrary. Arbitrary RF excitation pulse shapes in 2 or 3 dimensions based on the shape of the segmented structure can be used to further optimize the scan. In spectroscopy, optimization is achieved by maximizing the ratio of volume of interest to unwanted background in the selected volume, and the scanner provides this measure of optimality to the operator before acquisition.

It is contemplated that RF pulses that are selective in more than one direction may be employed so that axis information may be used more efficiently. For example, for selective pulses in a plane, the projection algorithm provides the projection needed to select a 2D excitation region, along with the required orientation. If the long axis (perpendicular to the plane) is chosen for the readout direction, this results in the most efficient prescription for imaging only the structure(s) of interest (in a single scan with Cartesian encoding). The 2D excitation may be rectangular or arbitrary. This may be useful for 2D scans such as BOLD EPI where only the activation of a particular structure such as the hippocampus is desired. In this case, optimizing the scan prescription also minimizes the repetition time; thus, maximizing the sampling rate of the BOLD signal. The flip angle can be adjusted spatially in relation to the anatomy by arbitrary RF pulse shaping such that local contrast can be manipulated within the ROI.

The optimized pulse sequence is then used to direct the MRI system to acquire an image (or spectroscopy data) in the usual fashion as indicated at process block 326. However, in this system illustrated in FIG. 2, the multiple RF transmitters 198 and associated coil elements in the array 155 are separately driven to produce RF excitation and RF saturation pulses that optimally select the structure of interest.

Referring back to FIG. 5, as indicated at decision block 328, multiple images with different prescribed pulse sequences can be acquired by looping back to process block 320.

Despite accurate positioning, spectral quality may still be compromised by a change in subject position between the localizer and the scan or during the spectroscopy acquisition. Under ideal conditions (no compartment transitions within the voxel, good shim and good water suppression), spectral line widths should be independent of voxel size and increase linearly with field strength. However, subject motion induces phase shifts that cause successive measurements to interfere destructively and broadens the lines. Some have described methods for retrospective phase correction. These methods also correct for scanner drift. However, the anatomical source of the signal may physically shift away from the actual target, and this can only be corrected by real-time methods. To correct for rigid body subject motions in real-time, it is contemplated that navigators may be inserted into the pulse sequence. A variety of navigators are contemplated for motion correction during these scans, including, for example, EPI or EVI-based, cloverleaf and the like.

In particular, the navigators may be implemented in the MPRAGE sequence by inserting them during the delay time (TD) after the partition encoding and before the following inversion. The implementation for spectroscopy is very similar as there is an equivalent delay after the FID and before the following excitation. In accordance with one embodiment, three spirals, one for each of the three orthogonal planes, was inserted in each TD.

The present invention has been described in terms of the various embodiments, and it should be appreciated that many equivalents, alternatives, variations, and modifications, aside from those expressly stated, are possible and within the scope of the invention. Therefore, the invention should not be limited to a particular described embodiment.

The invention claimed is:
1. A method for imaging a desired structure in a subject with a magnetic resonance imaging (MRI) system, the steps comprising:
   a) acquiring an image with the MRI system during a first session that depicts the desired structure;
   b) segmenting the acquired image to identify a position and boundary of the desired structure;
   c) prescribing a pulse sequence using the identified position and boundary produced in step b) to tailor a radio frequency (RF) pulse for application to the desired structure; and
   d) acquiring an image of the desired structure using the MRI system and the pulse sequence prescribed in step c).

2. The method of claim 1 wherein step c) includes:
   c)i) displaying the position and boundary identified in step b);
   c)ii) selecting, from the displayed position and boundary, the desired structure to be imaged; and
   c)iii) setting scan parameters in a selected pulse sequence based on the selected desired structure.

3. The method of claim 2 wherein the scan parameters set in step c)iii) includes a waveform of an RF pulse produced by each of a plurality of RF coils such that an RF magnetic field produced using the RF pulse waveform is positioned and shaped according to a position and shape of the selected desired structure.

4. The method of claim 1 further comprising the step of:
   e) between steps a) and b), acquiring alignment data with the MRI system during the first session that indicates a position of the subject during step a); and
   f) after step b), acquiring alignment data with the MRI system during a second session; and
   g) after step f) and before step d), aligning the subject in the first and second sessions using the alignment data acquired therein.

5. The method of claim 4 further comprising removing the subject from the MRI system between steps e) and f).

6. The method of claim 4 wherein step g) includes:
   g)i) relating left-posterior-superior (LPS) coordinates of the MRI system to column-row-slice (CRS) coordinates through a matrix ($M_{CRS \rightarrow LPS}^{seg}$) determined from a prescription of the MRI system given by an automated segmentation program, such that:

$$v_{LPS}^{seg} = M_{CRS \rightarrow LPS}^{seg} v_{CRS}^{seg}.$$

7. The method of claim 6 wherein step g) further includes:
   g)ii) relating the LPS coordinates of the MRI system to anatomical LPS coordinates using an AutoAlign matrix given by:

$$v_{AA/LPS} = (M_{AA}^{seg})^{-1} v_{LPS}^{seg}.$$

8. The method of claim 7 wherein step g) further includes:
   g)iii) using an AutoAlign matrix $M_{AA}$ determined using an AutoAlign procedure to relate the LPS coordinates of the MRI system for a given session to anatomical LPS coordinates, where:

$$v_{LPS} = M_{AA} v_{AA/LPS}.$$

9. The method of claim 1 wherein step b) further includes selecting an automated segmentation method including at least one of a centroid segmentation method, a bounding box segmentation method, a bounded box segmentation method, and a minimum projection segmentation method.

10. The method of claim 1 further comprising:
    e) repeating steps c) and d) to acquire multiple images with different prescribed pulse sequences selected for different desired structures in the subject.

11. A method for imaging a desired structure in a subject with a magnetic resonance imaging (MRI) system, the steps comprising:
    a) performing a first data acquisition session with the MRI system comprising:
       a)i) acquiring a first set of imaging data from a portion of the subject including the desired structure;
       a)ii) acquiring alignment data that indicates a position of the subject during the first data acquisition session;
    b) reconstructing a first image from the first set of imaging data acquired during step a);
    c) segmenting the first image to identify a position and boundary of the desired structure;
    d) performing a second data acquisition session with the MRI system comprising:
       d)i) acquiring alignment data that indicates a position of the subject during the second data acquisition session;
       d)ii) positioning the subject in the position of the subject during the first data acquisition session using the alignment data acquired during the first imaging session and the alignment data acquired during the second imaging session;
       d)iii) prescribing a pulse sequence based on the position and boundary of the desired structure identified in step c) to target the desired structure by using the identified position and boundary to tailor a radio frequency (RF) pulse for application to the desired structure;
       d)iv) acquiring a second set of imaging data from a portion of the patient including the desired structure using the MRI system and the pulse sequence prescribed in step d)iii); and
    e) reconstructing an image of the desired structure from at least the second set of imaging data.

12. The method of claim 11 further comprising removing the subject from the MRI system between steps a) and d).

13. The method of claim 11 wherein step c) further includes selecting an automated segmentation method including at least one of a centroid segmentation method, a bounding box segmentation method, a bounded box segmentation method, and a minimum projection segmentation method.

14. The method of claim 11 further comprising:
    f) repeating steps d)iii) and d)iv) to acquire multiple imaging data sets with different prescribed pulse sequences and tailored RF pulses selected for different desired structures in the subject.

15. The method of claim 11 wherein step d)iii) includes displaying the position and boundary of the desired structure identified in step c), selecting, from the display, the desired structure to be imaged, and setting scan parameters in a selected pulse sequence based on the selected desired structure.

16. The method of claim 11 wherein step a)ii) includes acquiring at least one of alignment scout image and a navigator signal.

17. The method of claim 11 wherein step d)i) includes acquiring at least one of an alignment scout image and a navigator signal.

* * * * *

UNITED STATES PATENT AND TRADEMARK OFFICE
CERTIFICATE OF CORRECTION

PATENT NO. : 8,831,703 B2
APPLICATION NO. : 11/977153
DATED : September 9, 2014
INVENTOR(S) : Andre van der Kouwe It is certified that error appears in the above-identified patent and that said Letters Patent is hereby corrected as shown below:

In the Specification

Column 6, line 32, Eq. (1), " $V_{AA/LPS} = \left(M_{AA}^{seg}\right)^{-1} v_{LPS}^{seg}$ " should be -- $V_{AA/LPS} = \left(M_{AA}^{seg}\right)^{-1} v_{LPS}^{seg}$ --.

Column 6, line 62, "$M_{CRS \rightarrow LPS}^{seg}$" should be -- $M_{CRS \rightarrow LPS}^{seg}$ --.

Column 6, line 67, Eq. (2), $v_{LPS}^{seg} = M_{CRS \rightarrow LPS}^{seg} v_{CRS}^{seg}$" should be -- $v_{LPS}^{seg} = M_{CRS \rightarrow LPS}^{seg} v_{CRS}^{seg}$ --.

In the Claims

Column 11, claim 6, line 18, "$M_{CRS \rightarrow LPS}^{seg}$" should be -- $M_{CRS \rightarrow LPS}^{seg}$ --.

Column 11, claim 6, line 22, "$v_{LPS}^{seg} = M_{CRS \rightarrow LPS}^{seg} v_{CRS}^{seg}$" should be -- $v_{LPS}^{seg} = M_{CRS \rightarrow LPS}^{seg} v_{CRS}^{seg}$ --.

Signed and Sealed this
Thirtieth Day of December, 2014

Michelle K. Lee
*Deputy Director of the United States Patent and Trademark Office*

CERTIFICATE OF CORRECTION (continued)
U.S. Pat. No. 8,831,703 B2

Column 11, claim 7, line 28, " $V_{AA/LPS} = \left(M_{AA}{}^{seg}\right)^{-1} v_{LPS}{}^{seg}$ " should be -- $V_{AA/LPS} = \left(M_{AA}^{seg}\right)^{-1} v_{LPS}^{seg}$ --.